United States Patent
Ardelt et al.

(10) Patent No.: US 8,649,006 B2
(45) Date of Patent: Feb. 11, 2014

(54) PLASMA EMISSION TRANSFER AND MODIFICATION DEVICE

(75) Inventors: Dirk Ardelt, Krefeld (DE); Klaus Sickelmann, Bedburg-Hau (DE); Petar Slavov Ivanov, Kleve (DE)

(73) Assignee: Spectro Analytical Instruments GmbH, Kleve (DE)

( * ) Notice: Subject to any disclaimer, the term of this patent is extended or adjusted under 35 U.S.C. 154(b) by 65 days.

(21) Appl. No.: 13/271,078

(22) Filed: Oct. 11, 2011

(65) Prior Publication Data

US 2013/0057858 A1    Mar. 7, 2013

(30) Foreign Application Priority Data

Sep. 6, 2011 (EP) .................................... 11007215

(51) Int. Cl.
*G01J 3/00*    (2006.01)
(52) U.S. Cl.
USPC .......................................................... 356/300
(58) Field of Classification Search
USPC ................................................ 356/300, 316
See application file for complete search history.

(56) References Cited

U.S. PATENT DOCUMENTS

| | | | |
|---|---|---|---|
| 5,731,872 A | 3/1998 | Falk | |
| 5,841,531 A | 11/1998 | Gliddon | |
| 6,122,050 A | 9/2000 | Rutzke | |
| 2001/0035187 A1* | 11/2001 | Smith et al. | 128/205.24 |
| 2009/0256459 A1 | 10/2009 | Liu | |
| 2011/0186419 A1* | 8/2011 | Song et al. | 204/164 |

OTHER PUBLICATIONS

Extended European Search Report Issued in EP 11007215.4 mailed Feb. 15, 2012.

* cited by examiner

*Primary Examiner* — Tarifur Chowdhury
*Assistant Examiner* — Abdullahi Nur
(74) *Attorney, Agent, or Firm* — Novak Druce Connolly Bove + Quigg LLP

(57) ABSTRACT

A Plasma Emission Transfer and Modification Device allowing for alteration of the plasma shape or characteristics for e.g. optimized viewing of relevant Plasma zones or improved coupling of a Plasma to the subsequent spectrometer optics, at the same time avoiding negative effects (e.g. heat transfer from the spectro-chemical source into subsequent system components) is described.

10 Claims, 2 Drawing Sheets

PLASMA EMISSION TRANSFER AND MODIFICATION DEVICE

BACKGROUND OF THE INVENTION

Figure 1:
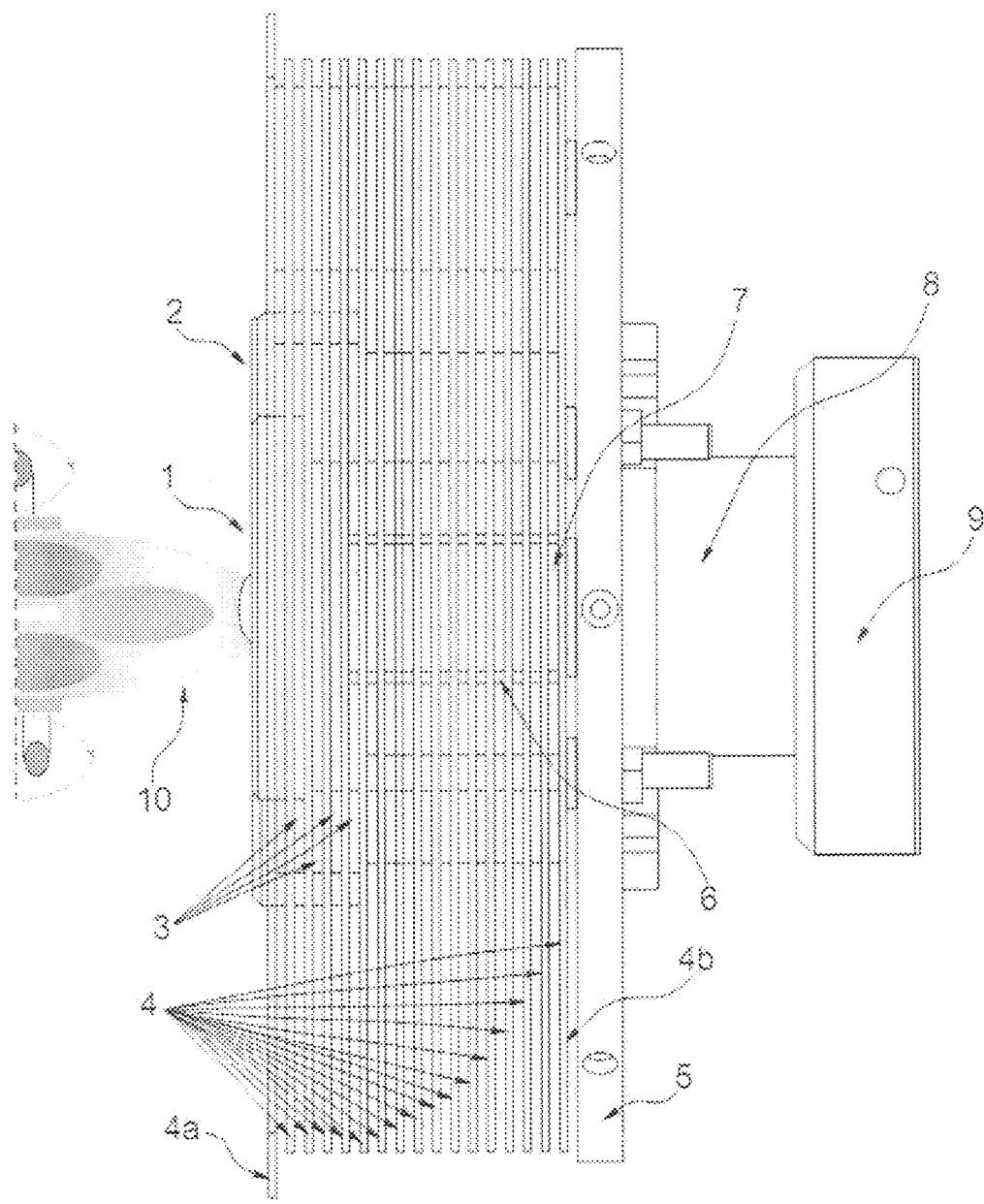

The present invention relates to the field of spectroscopy with a plasma source. Known, but in no way limiting implementations of plasma sources within the field of this invention are chemical flames, DC arc and spark plasmas, RF induced plasmas as e.g. an inductively coupled plasma (ICP) or microwave plasmas, at reduced, at atmospheric or above atmospheric pressure. The invention described can be used for optical emission spectroscopy, where the optical emission of any of the plasma sources described above is used as radiation source or in conjunction with plasma-source mass spectrometry, where any of the plasma sources described above is used as an ion source. Further uses of the invention described, e.g. in the field of plasma generation for materials processing can be conceived and do not limit the scope of the patent desired.

The use of suitable plasmas as spectroscopic sources is probably as old as spectroscopy itself. Already in 1859, Robert Bunsen and Gustav Kirchhoff invented the "spectroscope" and with it the method of emission spectroscopy, using a chemical flame as source, which already in 1860 allowed them to discover the formerly unknown chemical elements cesium and rubidium in mineral water, by their characteristic emission spectra. At those times, the spectro-chemical source was observed directly in air, without any additional means of coupling the source to the spectrometer for throughput improvement.

In the 1930s, electrical arc and spark sources became popular for optical plasma emission spectroscopy, together with the use of chemical flames. Latest with the development of the inductively coupled plasma (ICP) as spectroscopic source, by Greenfield and Fassel in the 1960s, chemical flames increasingly were replaced by electrical discharges using RF excitation to sustain the plasma, typically in a suitable inert gas, e.g. Argon, into which the sample is introduced in the form of a fine aerosol, generated e.g. by pneumatic nebulization. The first ICP sources, typically operating with RF excitation at 27 or 40 MHz, employed a vertically oriented plasma with a "radial" or side-on pick-up of the plasma-generated radiation to be transferred into a suitable spectrometer.

In the mid-1970s, the first ICP spectroscopy instruments were introduced commercially, using a vertically oriented plasma. In the mid-1970s, an ICP source with horizontal plasma orientation and end-on pick-up of the ICP generated radiation was developed and subsequently commercialized.

Compared to the radial plasma radiation pick-up of the vertical ICP, the axially viewed, horizontally oriented ICP allowed for significantly improved signal-to-background ratios, mainly due to the larger observable size of the emission region.

However, since optical radiation with photon energies above ca. 6.2 eV is readily absorbed by air, an efficient use of the complete energy range of the radiation produced by the source is not possible without additional coupling means. Especially for an axially viewed plasma source, it can additionally be advantageous to modify characteristics of the spectro-chemical source to further improve the transfer of desired source radiation, to suppress background radiation, or to adapt electrical properties. Examples of source characteristics to be modified include the geometrical shape of the plasma, the removal of outer, colder source regions or the change of an electrical plasma potential.

In the case of plasma source mass spectrometry, typically also employing a horizontally oriented ICP, an efficient ion transfer mandates a direct coupling of the source to the spectrometer.

Accordingly, technical solutions for advantageously modifying and coupling a horizontally oriented plasma source to a spectrometer's optical system are described e.g. in U.S. Pat. No. 5,731,872 "Plasma Manipulator", or specifically for a suitable modification of electrical plasma characteristics, in U.S. Pat. No. 5,841,531.

To fulfill the intended purpose, all technical solutions for modifying and coupling a horizontally oriented plasma source to a spectrometer's optical system require at least partial immersion of the device in the high temperature plasma. Typical spectro-chemical ICP sources, as an example, reach plasma temperatures of 6,000 -10,000K and are operated at RF powers between 1 and 2 kW.

A useable plasma modification and coupling device for a spectro-chemical plasma source thus requires a careful choice of material (e.g. resistance and electrical compatibility to the plasma environment), geometry (e.g. size and shape of the coupling device aperture, distance of the plasma coupling aperture from the spectrometer's optical system) and a suitable cooling (to avoid quick degradation of coupling device or optical components, or thermal instability of the spectrometer optics). So far, all known devices according to this purpose have been made from suitable conductive (metallic) material and have been liquid-cooled, specifically water-cooled. Not least due to the large heat capacity of typical, water-based cooling liquids, a very space-effective cooling of a plasma modification and coupling device for a spectro-chemical plasma source can be realized that further allows for device operation at or little above ambient temperature even at high plasma temperatures and powers, minimizing component wear and heat transfer to the spectrometer optics.

Increasingly, in the light of both environmental as well as economical concerns, liquid/water-cooling finds lessening acceptance. Additionally, liquid/water-cooling results in necessitating an additional resource for the operation of a plasma spectro-chemical device, unsatisfactory from a system complexity standpoint alone. Direct air-cooling of such device would be an ideal solution, however, due to the lower heat capacity of air, compared to water, achieving similar cooling power results in a larger heat exchanger and possibly higher operation temperatures for an air-cooled system.

Since the purpose of such plasma source modification and coupling device typically requires dimensioning of its size and positioning of optical elements in line with the source's or spectrometer's requirements, additional size or space constraints from a potentially larger air-air heat exchanger will typically result in less than optimal coupling. Additionally, higher operation temperatures, as often found in air-cooled systems can be detrimental for the performance and lifetime of delicate optical components, longer warm-up times (to reach a stable and higher operating temperature) negatively impact the long term stability of such device or an instrument incorporating such device. Both larger size and higher operation temperature are clearly undesirable for a spectro-chemical plasma modification and coupling device in the context of modern plasma spectro-chemical instrumentation.

Therefore, a need exists for a suitably air-cooled spectro-chemical plasma source modification and coupling device that replaces the undesirable liquid/water-cooling, remedying the presumed short-comings of air-cooled systems while preserving most or all advantageous aspects of existing implementations, most notably the optimum coupling geometry and the protection of the optical system from the high temperature plasma environment of the source.

SUMMARY OF THE INVENTION

The object of the invention is to provide a plasma source modification and coupling device for spectrochemical plasma sources, e.g. of the inductively coupled plasma type, which does not require additional cooling media apart from air and for which the air cooling neither does interfere with or limit dimensional requirements for an optimal optical coupling, nor leads to undesirable high operating temperatures. A safe operation of the device within the prescribed operating parameters has to be ensured by suitable means, e.g. safety interlocks or devices. Finally, undesirable properties of air-cooling, e.g. increased noise from high-speed airflows through small ducts have to be avoided.

In a plasma coupling device with a diaphragm of suitable material, optical or other elements to aid in the desired manipulation of plasma parameters and a structure to precisely position and keep the diaphragm and other elements in position, the object is achieved by providing a suitably dimensioned air cooling device which is thermally coupled to the diaphragm which constitutes a "hot end" of the cooling device. The cooling device further comprises a number of heat exchange plates which are spaced apart from each other to allow for an air flow between the plates and which are thermally connected in order to transfer heat from one cooling plate to another. The temperature of the cooling plates is therefore reduced from the hot end to a cold end, a number of cooling plates being provided between the two ends. The plasma source modification and coupling device further comprises a tubular structure supporting the optical elements and/or other elements to aid in the desired manipulation of plasma parameters, wherein the tubular structure is connected and held in position by the "cold end" of the air cooling device. The tubular structure, which in the case of an optical spectrometer can be called a "light tube", is thermally coupled to the cold end of the cooling device and thus held at a low temperature. The air-cooling device further provides a mechanical coupling, which allows mounting the whole device including the diaphragm and the light tube in a defined manner to the entrance of a spectrometer that is arranged to measure the desired properties of the plasma.

Mechanical stability and precision is further improved if the diaphragm and the light tube are directly connected to each other via a connecting element which is thermally insulating. This detail allows a mechanical coupling with sufficient stability.

Typical dimensions of a plasma used as a spectro-chemical source, e.g. an ICP, are in the range of 3 to 20 mm diameter, viewed from the diaphragm, thus all heat transfer between the up to 10,000K plasma and the immersed diaphragm occurs in a circular surface region with an area between ca. 30 and 1250 mm$^2$.

To avoid heat transfer from the immersed diaphragm to the light tube path (and thus to avoid any thermal stress on light tube or subsequent optical and system components), an air-cooling device in the form of a multiple-plates heat exchanger is mounted rigidly to the diaphragm, or to a suitable diaphragm mount, in a way to ensure good heat transfer between the diaphragm and the plate stack, e.g by an annular contact between the diaphragm or diaphragm mount and the plate stack and at the same time avoiding heat transfer into the light tube.

The multiple plates heat exchanger is designed in .a way that the cooling flow results in an axial temperature profile, i.e. a reducing temperature over the length of the stack, with the last plate reaching ambient or only slightly above ambient temperature. The multiple plates heat exchanger thus has a "hot end" (where the immersed diaphragm is mounted) and a "cold end" (where the heat exchanger preferably is mounted to a supporting structure.

Now, to avoid heat transfer between the multiple plates heat exchanger and the light tube, the heat exchanger and the annular heat transfer region have a central bore with a diameter larger than the light tube outer diameter, avoiding contact between the light tube and the (hotter than ambient) plates of the plate stack. To ensure the required geometrical precision in positioning the immersed diaphragm relative to the light tube (and thus included or subsequent optical elements), the immersed diaphragm is mounted with suitably high geometrical precision to the hot end of the multiple plates heat exchanger.

Furthermore, a rigid and precise mechanical connection of low thermal conductivity between the cold end of the multiple plates heat exchanger and the light tube (mount) is provided, allowing for a stable and precisely controlled geometrical relationship between the immersed diaphragm and light tube and/or subsequent optical system elements and at the same time efficiently avoiding heat flux into the light tube, ensuring stable and non-critical operation temperatures of light tube optical and subsequent system components.

Simulations and measurements show both the validity of the concepts described before and their implementation in an actual design fulfilling all requirements for a plasma emission transfer and modification device in the special case of an ICP-OES spectrometer. However, the invention is not limited to this specific implementation and can be applied for the modification of and emission transfer from spectro-chemical sources in many other obvious ways.

Figure 2:
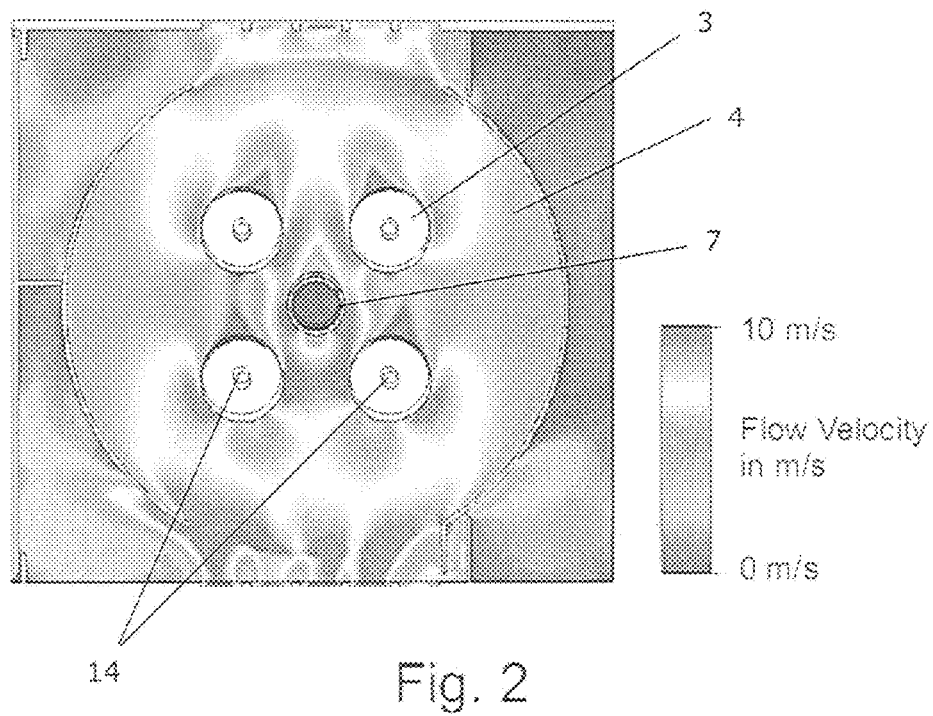
Figure 3:
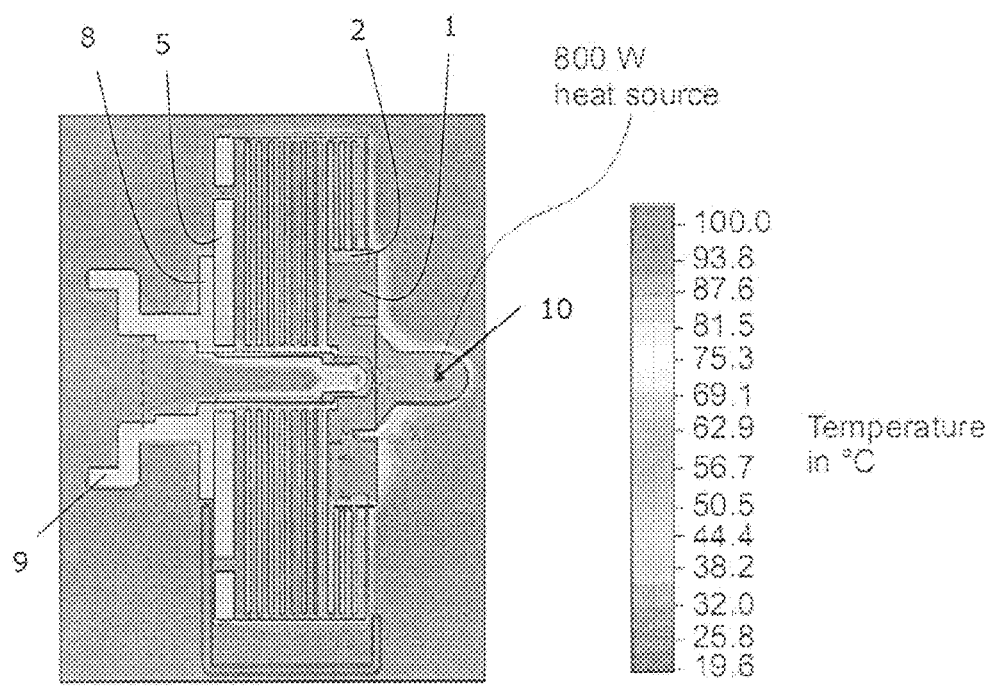

An embodiment of the invention is described in the following with regard to the drawing, in which FIG. 1 shows a side view of a cooling device with diaphragm and light tube;

FIG. 2 shows a CFD simulation of the flow velocities between two plates of the multiple plates heat exchanger; and FIG. 3 shows a CFD simulation of the resulting temperatures for the plasma source modification and coupling device with a multiple plates heat exchanger.

FIG. 1 shows a plasma modification and coupling device according to the present invention. The device comprises an embedded diaphragm 1 which is held and thermally contacted by a cylindrical diaphragm mount 2. The diaphragm mount 2 is provided with an outer annular surface, which dissipates the heat into a set of cooling plates 4. The cooling plates 4 are for example made of aluminum sheet metal. They have a flat, circular shape with a central bore. The cooling plates 4 are held at a certain distance by discs 3 which are interposed between the cooling plates 4. The discs are essentially like metal washers. The thickness of the discs 3 defines the distances between two adjacent cooling plates 4. The discs 3 are in mechanical and thermal contact with the cooling plates 4 and therefore transfer thermal energy from one cooling plate 4 to the next.

The assembly of cooling plates 4 and discs 3 is mechanically held together by bolts 14 which fix the assembly comprising the diaphragm 1, the diaphragm mount 2, the cooling plates 4 and the discs 3 to a mounting plate 5. The mounting plate 5 itself is fixed to a light tube mount 8 and a bayonet coupling 9. The bayonet coupling 9 is provided to fix the assembly as described above to the entrance of a scientific instrument, like a UV-spectrometer or a mass spectrometer.

For the purpose of this description, the spectrometer is assumed to be a UV-Spectrometer. The tubular structure will therefore be called a light tube.

A light tube mount 8 carries a light tube 7, which is mounted in a thermally conductive way to the light tube mount 8. The light tube 7 itself is coaxial to the light tube mount 8, the cooling plates 4 and the diaphragm 1. To avoid any contact between the light tube 7 and the cooling plates 4, the central bore of the cooling plates 4, as mentioned above, is of a larger diameter than the outer diameter of the light tube 7. Therefore, no heat can be transferred from the cooling plates 4 to the light tube 7 directly.

On the other end of the device, which is oriented away from the light tube mount 8, the light tube 7 is connected to the diaphragm 1. This connection serves to mechanically fix the light tube 7 relative to the diaphragm 1 and to seal a gap between the light tube 7 and the diaphragm 1 in order to achieve a well-defined space within the light tube and the diaphragm. The whole arrangement is co-axial to a spectrochemical source 10, which in the case of FIG. 1 is an ICP-source.

Effectively the light tube 7 "looks" through the central opening in the diaphragm 1 into the central region of the ICP-source 10. Any light which is emitted in the central region of the ICP-source can therefore be transferred throw the diaphragm 1 and the light tube 7 into the instrument which is coupled to the bayonet coupling 9 and can then be analyzed accordingly.

The connection between the light tube 7 and the diaphragm 1 is thermally non-conductive. The heat, which is generated by the spectro chemical source 10, is absorbed by the diaphragm 1 and then transferred to the diaphragm mount 2, but not to the light tube 7. From the diaphragm mount 2, the heat dissipates into the cooling plates 4 directly or through the thermally conductive discs 3. An airflow, which is directed through the stack of cooling plates 4, can then carry away the thermal energy. Since the heat is introduced into the stack of cooling plates 4 on the left hand side of FIG. 1 in the vicinity of the diaphragm 1, the left side of FIG. 1 can be called the hot end. It is also obvious that the temperature in an equilibrium state drops from left to right in FIG. 1, so that the cooling plate 4, which is closest to the mounting plate 5, is also the coldest cooling plate in operation. The light tube 7 which is in thermal contact with the light tube mount 8, is essentially held on that low temperature level because no significant amount of thermal energy is transferred from the diaphragm 1 to the light tube 7. The components within the light tube 7 are therefore at a low temperature level while the instrument is in operation. This low temperature level is essential for a stable operation of the whole instrument.

Thus, the plasma modification and coupling device consists of a tubular light tube 7, which by suitable means is removable for service purposes, but in operation is rigidly coupled to the optical system of the ICP-OES, e.g. by means of a bayonet 9. The light tube 7 may contain additional optical elements, e.g. a lens, for efficient radiation transfer from the quantity-modified spectro-chemical source (e.g. the ICP, in ICP-OES) into the subsequent optical system, e.g. a spectrometer allowing for a wide spectral wavelength coverage and simultaneous registration of all wavelengths emitted from the source. Furthermore, the light tube 7 may contain fluidic components to aid in the desired plasma modification or to efficiently transfer the radiation emitted by the spectrochemical source.

FIGS. 2 and 3 show the distribution of air flow velocities and temperatures for an implementation of a plasma emission transfer and modification device in the special case of an ICP-OES spectrometer using a multiple plates heat exchanger, designed to fulfill the feature requirements as described before.

For efficient cooling by a multiple plates heat exchanger that does not adversely affect geometrical requirements for efficient plasma modification and/or emission transfer, a sufficient flow around the plate stack is required. At the same time, turbulence, due to the resulting increase in flow noise, is generally not desirable.

A measure for the turbulence of a flow is the Reynolds number, Re, which in the general case is calculated according to:

$$Re = \frac{u_m d}{v}$$

with: $u_m$: mean flow velocity, d: characteristic dimension (e.g. diameter for a tube), v: kinematic viscosity of the fluid.

A flow is called 'turbulent' with a Reynolds number >2,300 for a cylindrical tube and >100,000 for flow over a plate. The multiple plates heat exchanger has flow channels of approximately rectangular geometry, consisting of single plates mounted in a distance of 1 to 5 plate thicknesses. The expected critical Reynolds number for this setup is thus expected to lie between 2,300 and 100,000, most probably nearer to 2,300 than 100,000.

For a rectangular channel the characteristic dimension d is the 'hydraulic diameter' $d_h$, calculated from the channel width b and height h according to:

$$d_h = \frac{2bh}{b+h}$$

Now, for the implementation of the multiple plates heat exchanger with circular plates and with a central bore to accommodate the light tube, the assumption of a rectangular channel might not be perfectly valid, but is an acceptable starting point for assessing the flow characteristics via the Reynolds number (which by itself is more 'qualitative').

Using the dimensions b=120 mm, h=2 mm, a hydraulic diameter $d_h$=3.9 mm results for a single channel between two plates of the multiple plates heat exchanger. With an average flow velocity of 5 m/s, as taken from the CFD simulation flow velocity results in FIG. 2, a Reynolds number Re of ca. 1300 results. The flow is thus expected to be non-turbulent. Up to flow velocities of ca. 8.8 m/s, Re stays below 2,300, and the flow thus remains non-turbulent.

Even for the highest flow velocities found, 10 m/s, Re is ca. 2,600, only slightly above the critical Re for a cylindrical tube. With the discussion above, for the multiple plates heat exchanger geometry, it is expected that even in these regions the flow remains mainly non-turbulent, i.e. the critical Re is most probably above 2,600.

A CFD simulation of the resulting temperatures for the plasma source modification and coupling device with a multiple plates heat exchanger fulfilling the above requirements are shown for a spectro-chemical source-caused heat load onto the immersed diaphragm of 800 W.

It can clearly be seen that the light tube, the mounting structure, the optical elements both inside the light tube and subsequent components mounted to the coupling stay at or near room temperature. The multiple plates heat exchanger does not influence any geometrical requirements for an efficient coupling of the spectro-chemical source emission to a subsequent optical system. Furthermore, the chosen design avoids heat transfer from the immersed diaphragm onto the light tube, while not requiring any cooling fluids other than air. These features are validated on an actual device, built according to the am requirements and used for optical emission spectroscopy with an inductively coupled plasma.

In summary, a preferred embodiment of the invention comprises some or all of the following features:

- A diaphragm of suitable material, suitably immersed in the plasma of the spectro-chemical source, suitably dimensioned to allow for the desired manipulation of plasma properties, e.g. size of a aperture with a reduced free diameter, compared to the plasma diameter, to mask of plasma regions only contributing to background signals.
- Optical and/or other elements to aid in the desired manipulation of plasma parameters and to allow for an efficient transfer of the interesting quantity of the spectro-chemical source after the manipulation, e.g. a lens if the desired quantity is optical radiation emitted from a spectrochemical plasma source. Other examples may include fluidic components, e.g. to produce a counter gas flow to allow for a continuously inert gas flushed light path from the relevant source regions into the spectrometer, or electrical components.
- A structure to precisely position and keep the a.m. diaphragm and other elements in position.
- A suitably dimensioned air cooling device, so that the cooling requirements are not limiting or negatively impacting dimensional requirements for an efficient plasma manipulation or plasma quantity transfer, e.g. focal length of optical elements (e.g. lens for radiation transfer from the manipulated spectro-chemical source into the spectrometer). This is typically achieved when the length of the light tube is not determined by the requirements of the air cooling device, but from e.g. the focal length of an optical element for emission transfer or the F/#-requirements of a subsequent optical system in the case of optical spectroscopy. Furthermore, the cooling device must be capable of ensuring that the operating temperature is below any critical temperature for any materials or components employed.
- Safety devices to ensure safe operation of the plasma source modification and coupling device within the parameters range allowable for the employed materials or components.

While a possible implementation of the plasma source modification and coupling device with a multiple plates heat exchanger for optical emission spectroscopy with an inductively coupled plasma (ICP-OES or ICP-AES) has been described, the described implementation in no way limits the scope of this invention, as is obvious to anybody skilled in the art.

The invention claimed is:

1. A plasma source modification and coupling device, including: a diaphragm disposed between a plasma source and one or more optical or other elements configured for the manipulation of plasma parameters; a support to precisely position and keep the diaphragm and other elements in position; and an air-cooling device thermally coupled to the diaphragm, wherein the air-cooling device comprises a number of cooling plates which are thermally connected in order to transfer heat from one cooling plate to another, and which are spaced apart from each other to allow for an air flow between the cooling plates.

2. The device according to claim 1, wherein the cooling plates are arranged in a stack, and wherein, in the stack, a distance between the cooling plates is 1 to 5 times a thickness of the cooling plates.

3. The device according to claim 1, wherein the cooling plates have a bore sufficiently large to accommodate a tube without contacting it.

4. A spectrometer with a device according to claim 1.

5. A plasma source modification and coupling device, including: a diaphragm disposed between a plasma source and one or more optical or other elements configured for the manipulation of plasma parameters; a support to precisely position and keep the diaphragm and other elements in position; and an air-cooling device thermally coupled to the diaphragm, wherein cooling plates are arranged in a stack such that in operation, when the diaphragm is subjected to a heat source, a temperature gradient is established through the stack, and such that, in operation, the diaphragm is adjacent to a hot end of the stack, while the support is adjacent to a cold end.

6. The device according to claim 5, wherein a tube is provided to support optical elements and/or other elements to aid in manipulation of plasma parameters.

7. The device according to claim 5, wherein a tube is connected and held in position by the support close to a cold end of the air-cooling device.

8. The device according to claim 5, wherein a tube is thermally coupled to a cold end of the air-cooling device.

9. The device according to claim 5, wherein the air-cooling device further includes a mechanical coupling, which allows mounting the device including the diaphragm and a tube in a defined manner to an entrance of a spectrometer that is arranged to measure one or more desired properties of the plasma.

10. The device according to claim 5, wherein the diaphragm and a tube are directly connected to each other via a connecting element, which is thermally insulating.

* * * * *